(12) United States Patent
Ecarma

(10) Patent No.: US 6,998,142 B2
(45) Date of Patent: Feb. 14, 2006

(54) COMPOSITION AND METHOD FOR THE PREVENTION AND TREATMENT OF ASTHMA

(76) Inventor: Virgilio Verzosa Ecarma, 259 Dona Soledad Avenue Extension Better Living Subdivision, Paranaque (PH), 1711

(\*) Notice: Subject to any disclaimer, the term of this patent is extended or adjusted under 35 U.S.C. 154(b) by 67 days.

(21) Appl. No.: 10/450,170

(22) PCT Filed: Dec. 13, 2001

(86) PCT No.: PCT/PH01/00007

§ 371 (c)(1),
(2), (4) Date: Jun. 11, 2003

(87) PCT Pub. No.: WO02/49659

PCT Pub. Date: Jun. 27, 2002

(65) Prior Publication Data

US 2004/0047929 A1 Mar. 11, 2004

(30) Foreign Application Priority Data

Dec. 19, 2000 (PH) .................................... 1-2000-03505

(51) Int. Cl.
*A61K 35/78* (2006.01)

(52) U.S. Cl. ........................ 424/779; 424/773; 424/725
(58) Field of Classification Search ................ 424/725, 424/195.1, 773, 774, 779
See application file for complete search history.

(56) References Cited

FOREIGN PATENT DOCUMENTS

| JP | 60-126225 | * | 7/1985 |
|---|---|---|---|
| PH | 29242 A | * | 5/1993 |
| PH | 27501 | | 8/1993 |
| PH | 29242 | | 1/1997 |
| PH | 30978 | | 12/1997 |

OTHER PUBLICATIONS

Chin, F, J., Hospitals Take a Deep Breath//UCI/CHOC Join Forces to Open the Asthma Chronic Lung Disease Center in an Effort to Reduce Emergency Room Visits by Young Asthma Patients; Orange County Register, Santa Ana, CA, Feb. 14, 2004, pp. 1–3.*

Parker, M The Asthma Society of Canada Recognizes the Ability of Sharp's Plasmacluster Ion Technology to Reduce Airborne Asthma and Allergy Triggers; Canada News Wire, Ottawa May 3, 2003, pp. 1–3.*

Palaypayon, C.M The Philippine Narra: A Potential Cure for Cancer; Canopy International vol. 26, No. 3, May to Jun. 2000, pp. 1–2.*

\* cited by examiner

*Primary Examiner*—Patricia Leith
(74) *Attorney, Agent, or Firm*—Moazzam & Latimer LLP

(57) ABSTRACT

A pharmaceutical formulation for oral administration containing root, bark and wood of Philippine Narra tree (*Pterocarpus Indicus*) in dried powder form in sachet in a unit of (2) to (3) grams and made into a decoction of (8) ounces or in capsule in a unit of (100) to (300) milligrams at a dosage of three to six times a day can enhance the immune system of a person and can be used for the prevention and treatment of ASTHMA.

8 Claims, No Drawings

COMPOSITION AND METHOD FOR THE PREVENTION AND TREATMENT OF ASTHMA

FIELD OF THE INVENTION

The present invention is directed to the decoction or as capsule of the root, bark and wood of the Philippine Narra tree (*Pierocarpus Indicus*) when taken three to six times a day to enhance the immune system and used for the prevention and treatment of ASTHMA.

BACKGROUND OF THE INVENTION

The applicant/inventor was awarded by the Philippine Bureau of Patents, Trademarks and Technology Transfer with Patents Nos. 27501, 29242, and 30978 for a pharmaceutical formulation for the oral administration containing bark and wood of the Philippine Narra tree (*Pterocarpus Indicus*) in dried powder form in a unit dosage from 1 to 5 grams which is effective for the treatment of diabetes mellitus, arthritis, hypertension and stone in the bladder. The Philippines Narra tree (*Pterocarpus Indicus*) has been used by the applicant/inventor as treatment for his Rheumatoid Arthritis. After years of use, it became apparent that the Philippine Narra can also enhance the immune system and the applicant/inventor has successfully treated immunosuppressed persons (HIV/AIDS patients) with it.

In this regard the applicant/inventor has applied with the Philippine Bureau of Patents, Trademarks and Technology Transfer for an Invention Patent entitled A METHOD USING THE PHILIPPINE NARRA TREE (*PTEROCARPUS INDICUS*, WILLD) AS HERBAL MEDICINE FOR THE ENHANCEMENT OF THE IMMUNE SYSTEM AND USED AS TREATMENT FOR HVI/AIDS, which is still pending.

The function of the immune system is to defend the body against invaders like viruses, fungi, cancer cells and other substances foreign to the body thus the body's immune system attacks and eliminates not only bacteria and other foreign substances but also cancer cells. The immune system's critical role in controlling cancer cell development is exemplified by an astounding statistic: Cancer is 100 times more likely to occur in people who take drugs that suppress the immune system (for example, because of an organ transplant or a rheumatic disease) than in people with normal immune systems. Moreover, it has been found that blood glucose is necessary for tumor and cancer cells to grow and proliferate. If blood glucose is considerably reduced; the cancer cells will wither and die. Philippine Narra has the property of lowering the blood glucose and also the property of enhancing the immune system of immunosuppressed persons (HIV/AIDS) which make it ideal to effectively treat cancer. In this regard the applicant/inventor has also applied with the Philippine Bureau of Patents, Trademarks and Technology Transfer for an Invention Patent entitled THE PHILIPPINE NARRA TREE (*Pterocarpus Indicus*, Willd.) AS HERBAL MEDICINE FOR THE TREATMENT OF CANCER, which is still pending. Although the immune system is intricate, its basic strategy is simple: to recognize the enemy, mobilize forces, attack and clean up the scene of the battle. Much of the immune system's machinery is geared toward killing or eliminating invading microbes once they have been recognized. Sometimes the immune system malfunctions, misinterprets the body's tissues as foreign, and attacks them. Immune reactions are characterized by inflammation, which is normally a repair process and subsides when the repair is completed A Community Based Health Program (an NGO) invited the applicant/inventor to share his above-mentioned formulation for free to the less fortunate inhabitants of Barangay Tala, Kaloocan City. This is for the various illnesses that the formulation is suited for. Because the applicant/inventor patented invention shows that it can boost the immune system, many diseases were alleviated such as colds, flu, skin infections, acne, urinary track infections, respiratory infections including ASTHMA, cysts, and many other infectious diseases including leprosy.

ASTHMA is defined as a "disease characterized by an increased responsiveness of the trachea and bronchi to various stimuli, and manifested by widespread narrowing of the airways that changes in severity either spontaneously or as a result of treatment" (American Thoracic Society). About 5% of the population suffer from asthma. The pathogenesis of asthma is poorly understood. Multiple complex immune system mechanisms probably are involved Numerous cytokines derived from tissue mast cells, eosinophils, T lymphocytes, macrophages, neutrophils, and other lung cells are critical in initiating and perpetuating the asthmatic response and play important roles in the immunopathogenesis of airways inflammation (*CURENT Medical Diagnosis & Treatment* $36^{th}$ Edition). In persons with asthma, the airways narrow (bronchoconstriction) in response to stimuli that don't affect the airways of normal lungs. The narrowing can be triggered by many stimuli (an allergen), such as pollens, dust mites, animal dander, smoke, cold air, and exercise. Bronchodilator drugs that relieves attacks of asthma that acts on all beta-adrenergenic receptors such as adrenaline cause side effects such as rapid heartbeat, restlessness, headache, and muscle tremors. Theophylline is another bronchodilator drug whose administration must be closely monitored by a doctor, because too little drug in the blood may give little benefit, and too much drug may cause life-threatening abnormal heart rhythms or seizures and patients may also experience insomnia, agitation, and vomiting. Corticosteroids drugs are exceptionally effective at reducing asthma symptoms by blocking the body's inflammatory response but long term use may result in poor wound healing, loss of calcium from the bones, stomach bleeding, premature cataracts, elevated blood sugar levels, hunger, weight gain, mental problem, and stunted growth in children.

It has now surprisingly been found out that our Philippine Narra (*Pterocarpus Indicus*) has exhibited unexpectedly some pharmacological properties that can prevent and treat asthma.

SUMMARY OF THE INVENTION

The invention relates to the discovery of the medicinal value of the root, barks and wood of the Philippine Narra tree (*Pterocarpus indicus*) in decoction or powder form to enhance the immune system and used for the prevention and treatment of asthma. The advantages of this are that it has no side effects, it is affordable, and it is easy to manufacture. Other advantageous features of this invention will become apparent from the reading of the following detailed description.

DETAILED DESCRIPTION OF THE INVENTION

The newly cut root, bark, and wood of the Philippine Narra tree (*Pterocarpus Indicus*) are scrubbed of any dirt and extraneous materials. It is washed twice with clean water and again washed with chlorinated water of 20 PPM of Chlorine.

It is air dried for several weeks. It is grounded to a powder form and dried in an oven to a moisture content of less than 10%.

One process is to pack the powder form in capsules at 100 to 300 milligrams each.

Another process is to pack the powder form in sachet at 2 to 3 grams each.

Another process is to boil for at least 15 minutes the powder form at 2 to 3 grams per 8 ounces of water and store the decoction in sterile bottle and refrigerate.

The applicant/inventor using the above formulation from Philippine Narra has treated more than thirty (30) patients suffering from asthma and 90% of them were cured. Likewise, Dr. Rene Bautista, M.D. reported that 100% of his patients suffering from asthma were cured after administering them with the above formulation from Philippine Narra.

Thus, the invention includes a pharmaceutical formulation from the root, bark, and wood of the Philippine Narra tree (*Pterocarpus indicus*) in dried powder form in a sachet of 2 to 3 grams, which is made into a decoction and administered in an effective dosage to enhance the immune system, and which can be used for prevention and treatment of asthma. Likewise, the invention includes a pharmaceutical formulation from the root, bark, and wood of the Philippine Narra tree (*Pterocarpus indicus*) in dried powder form in a capsule of 100 to 300 milligrams and administered in an effective dosage to enhance the immune system, and which can be used for prevention and treatment of asthma.

The invention claimed is:

1. A method of treating a subject suffering from asthma, comprising administering to the subject in need thereof, a pharmaceutical formulation comprising a dried powder of root, bark and wood of the Philippine Narra tree (*Pterocarpus indicus*) or a decoction of said powder.

2. The method of claim 1, wherein said administering comprises orally ingesting a capsule containing 100 mg to 300 mg of a cleaned, ground, dried powder of the root, bark and wood of *Pterocarpus indicus* three to six times per day.

3. The method of claim 1, wherein the formulation comprises 2 to 3 grams of a cleaned, ground, dried powder of the root, bark and wood of *Pterocarpus indicus*.

4. The method of claim 1, wherein the formulation is in the form of a sachet.

5. The method of claim 1, wherein the formulation is in the form of a capsule.

6. The method of claim 1, wherein said administration prevents the patient from having an asthma attack.

7. The method of claim 1, wherein said formulation comprises a capsule containing 100 mg to 300 mg of a cleaned, ground, dried powder of the root, bark and wood of *Pterocarpus indicus*.

8. The method of claim 1, wherein said administering comprises orally ingesting the decoction containing 2 to 3 grams of a cleaned, ground, dried powder of the root, bark and wood of *Pterocarpus indicus* three to six times per day.

* * * * *